United States Patent
Ishii et al.

(10) Patent No.: US 7,108,134 B2
(45) Date of Patent: Sep. 19, 2006

(54) SAMPLE PACKING COVER BODY FOR SINGLE ARTICLE STORAGE DISPLAY FOR SALES PROMOTION PURPOSE

(75) Inventors: Shinichi Ishii, Tokyo (JP); Nobuya Koujitani, Tokyo (JP)

(73) Assignee: Uni-Charm Corporation, Ehime-Ken (JP)

( * ) Notice: Subject to any disclaimer, the term of this patent is extended or adjusted under 35 U.S.C. 154(b) by 117 days.

(21) Appl. No.: 10/241,003

(22) Filed: Sep. 10, 2002

(65) Prior Publication Data

US 2003/0066775 A1 Apr. 10, 2003

(30) Foreign Application Priority Data

Sep. 10, 2001 (JP) ............................. 2001-274233

(51) Int. Cl.
*B65D 85/08* (2006.01)
(52) U.S. Cl. ...................... 206/440; 206/471; D9/624; 604/385.02
(58) Field of Classification Search ........ 206/438–440, 206/471, 461, 494; 604/385.01, 385.02, 604/385.06, 385.17; D9/624, 627, 628, 631, D9/720–722; D2/711, 713, 864, 863; D3/205
See application file for complete search history.

(56) References Cited

U.S. PATENT DOCUMENTS

| | | | | |
|---|---|---|---|---|
| 3,837,476 A | * | 9/1974 | Schwartz | 206/45.24 |
| D255,328 S | * | 6/1980 | Carroll | D9/722 |
| D282,819 S | * | 3/1986 | Laurent et al. | D9/624 |
| 4,579,556 A | * | 4/1986 | McFarland | 604/385.26 |
| 4,631,062 A | * | 12/1986 | Lassen et al. | 604/385.02 |
| 4,653,642 A | | 3/1987 | Hakun et al. | |
| 4,674,135 A | * | 6/1987 | Greene | 2/400 |
| 4,795,029 A | * | 1/1989 | Campbell et al. | 206/278 |
| 4,804,380 A | * | 2/1989 | Lassen et al. | 604/385.17 |
| 4,917,675 A | * | 4/1990 | Taylor et al. | 604/385.02 |
| 5,098,422 A | * | 3/1992 | Davis et al. | 604/385.04 |
| 5,259,503 A | * | 11/1993 | Steingraber, Jr. | 206/440 |
| 5,261,531 A | | 11/1993 | Nieves | |
| D361,932 S | * | 9/1995 | Hensch | D9/623 |
| 5,485,919 A | * | 1/1996 | Samberg et al. | 206/461 |
| D381,898 S | * | 8/1997 | Craig | D9/621 |
| 5,813,546 A | * | 9/1998 | Wilson et al. | 211/32 |
| 5,845,778 A | | 12/1998 | Hickey, Jr. | |
| 5,854,733 A | * | 12/1998 | Jerkins | 361/212 |
| 5,928,184 A | * | 7/1999 | Etheredge et al. | 604/15 |
| 6,423,043 B1 | * | 7/2002 | Gustafsson | 604/385.01 |
| 6,772,446 B1 | * | 8/2004 | Black | 2/406 |

FOREIGN PATENT DOCUMENTS

| | | |
|---|---|---|
| DE | 2 414 064 | 10/1974 |
| DE | 197 01 574 | 7/1998 |
| JP | A-9-135862 | 5/1997 |
| WO | WO 97/49618 | 12/1997 |
| WO | WO 00/13632 | 3/2000 |

* cited by examiner

Primary Examiner—Jila M. Mohandesi (57) ABSTRACT

It is an object of the invention to make a single article storage display capable of fully showing performance or an appealing point to consumers. A portion of a sample packing cover member, in which a part of a sanitary napkin to be brought into contact with a wearer faces the portion while the napkin is housed in the cover member, is made transparent. The transparent portion is given curvatures in both longitudinal and lateral directions such that a contour of the transparent portion faithfully follows a contour of the sanitary napkin, thereby making it easy for a user to ascertain the contour of the sanitary napkin.

12 Claims, 6 Drawing Sheets

SAMPLE PACKING COVER BODY FOR SINGLE ARTICLE STORAGE DISPLAY FOR SALES PROMOTION PURPOSE

BACKGROUND OF THE INVENTION

1. Field of the Invention

The invention relates to a single article storage display for sales promotion purpose with regard to a certain article; for example, a sanitary napkin, a sanitary pad, or a sanitary panty, and incontinence articles, such as an incontinence underwear or an incontinence pad. Particularly, the invention relates to a single article storage display comprising a sample packing cover member suitable for packing a sample of a commodity product relating to an article and to a sample of commodity product packed with the sample packing cover member.

2. Related Art

A sanitary napkin is of old origin and can be traced back to napkins used in World War I for stopping the flow of blood in wounded soldiers. Therefore, for a number of years flat sanitary napkins very similar to those used on the battlefield were used. Recently, various sanitary napkins having a variety of shapes and kinds have been developed according to absorbing ability and applications, and such napkins are available on the market.

Various efforts have been made to clearly describe the performance and application of a commercial sanitary napkin. Most of these descriptions are effected by literal conveyance of information. However, users are unfamiliar with literal descriptions because of use of technical terms, which render the descriptions difficult to understand or difficult to read. These days, people no longer read as much as they used to and tend to avoid literal descriptions.

For these reasons, to the extent possible, the manner of application and performance of the napkin are preferably made visual and ascertainable at a glance.

Figure 13:
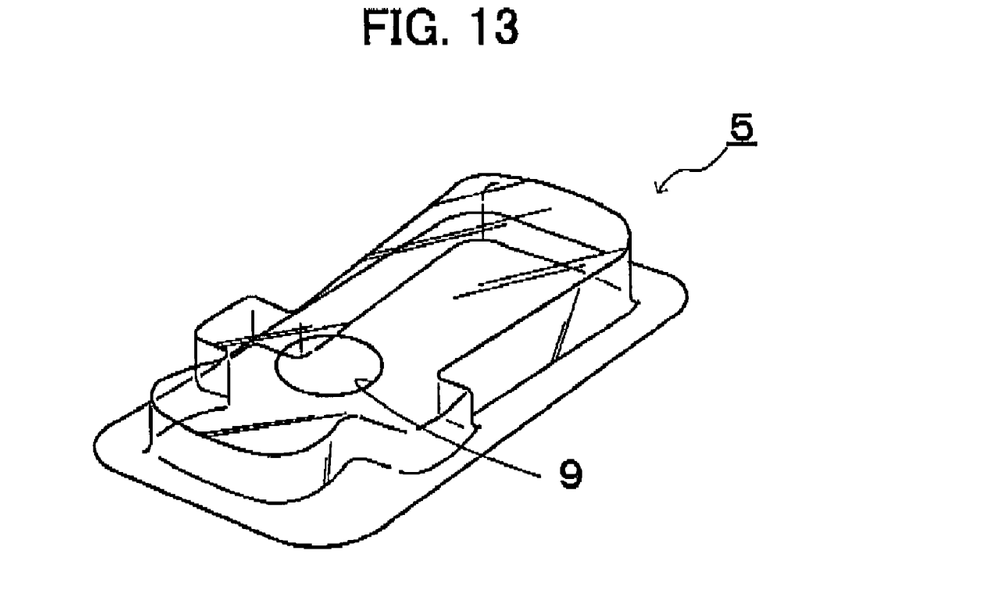
FIG. 13 is a perspective view showing a related-art sample packing cover member.
Figure 14:
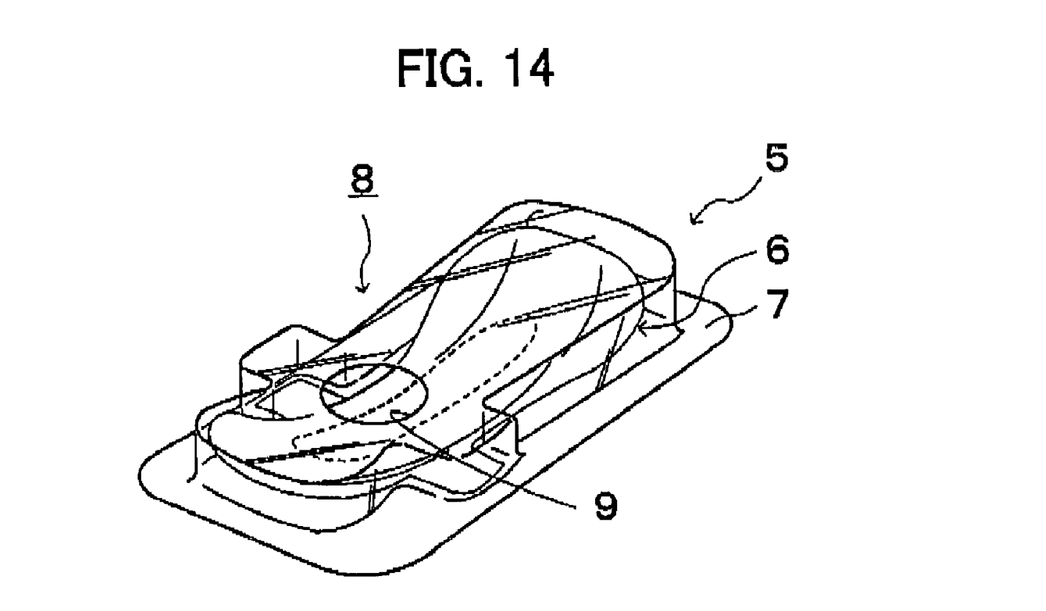
FIG. 14 is a perspective view showing a single article storage display formed by means of packing a sample commodity product (that is a sanitary napkin) in a related-art sample packing cover member.

However, the performance of a sanitary napkin is not actually indicated in a visual manner. Under these circumstances, the following is practiced. Specifically, a sample product 6 is housed in a transparent case body 5, such as that shown in FIG. 13, and the back of the transparent case body 5 is sealed with a board art 7, thereby forming a single article storage display 8 (see FIG. 14). The display is hung at the side of a showcase.

Even when such a single article storage display 8 is used, a conventional single article storage display appeals to users to only a small extent in connection with the performance of a commodity product and others. In terms of usefulness as a sales promotion tool for arousing the consumers' appetite for buying products, such a display is insufficient.

The invention has been conceived in light of the foregoing problems and aims at making a single article storage display capable of fully providing performance or an appealing point to consumers. More specifically, there is provided a sample packing cover member which enables production of such a single storage display.

SUMMARY OF THE INVENTION

To achieve the object, the invention is characterized in that a portion of a sample packing cover member, in which a portion of a sanitary napkin to be brought into contact with a wearer faces the portion while the napkin is housed in the cover member, is made transparent and in that the transparent portion is imparted with curvatures in both longitudinal and lateral directions such that a contour of the transparent portion faithfully follows a contour of the sanitary napkin, thereby making it easy for a user to ascertain the contour of the sanitary napkin. Further, the invention is characterized by preventing deviation of a sample product housing in a sample packing cover member, which would otherwise be caused when the display is handled roughly by a consumer.

Moreover, the sample packing cover member is provided with a sub-display piece for further enhancing a point appealing to the consumer or with an auxiliary display piece for causing the consumer to specifically recall a state in which the consumer wears the product.

More specifically, the invention provides the following:

(1) A sample packing cover member which acts as a cover of a single article storage display to be used for sales promotion of certain products, such as sanitary products or incontinence products, wherein, provided that a portion of the cover member (a human-body-contact-side cover portion) which, when the product is packed, covers a side of a certain product (that is a human-body-contact surface side), the side acting as a contact surface (a human-body-contact surface) to be brought into contact with a wearer, is transparent and that a direction coincident with a direction of a pudendal cleft of labia of the wearer is taken as direction "x" and a direction orthogonal to the direction of pudendal cleft of labia of the wearer is taken as direction "y,"

a curvature is formed in at least the direction "y," thereby giving the impression that the entire single article storage display has a concave shape when the single article storage display is viewed from the outside.

Formed in the sample packing cover member as defined in (1) is a curvature which gives the impression that the entire single article storage display has a concave shape in the direction orthogonal to the direction of a pudendal cleft of labia of the wearer. As a result, depressions and protrusions formed in the surface of a sanitary napkin which are present in the direction orthogonal to the pudendal cleft are shown to the consumer in an exaggerated manner.

By means of such a construction, when a single article storage display is formed by packing a sanitary napkin which is to be inserted deeply into the pudendal cleft or the cleft of buttocks so as to prevent leakage of menstrual blood, a consumer who has picked up the article for observation can readily understand the performance of the napkin at a glance. Hence, such a display provides great advantages in appealing to a consumer who places a primary concern on prevention of leakage of menstrual blood to readily choose a commodity product.

By means of the curvature formed in such a direction, gathers provided for preventing lateral leakage of menstural blood from a sanitary napkin are readily raised. Such a display is convenient for the consumer to ascertain the performance of the gathers.

Here, the expression "a curvature gives the impression that the entire single article storage display has a concave shape when the single article storage display is viewed from the outside" provides the following meanings. In principle, the product has an actually concave shape. When viewed from the outside, the product gives the impression that the entirety of the product has a concave shape. However, there is no necessity for all the related portions to have a concave shape. A portion of the product may have a protuberance, so long as the product gives the impression that the entire single article storage display has a concave shape.

(2) The sample packing cover member described in (1) is further characterized in that a curvature for giving the impression that the entire single article storage display has a concave shape when the single article storage display is viewed from the outside is formed also in the "x" direction.

The sample packing cover member (2), in which the curvature is formed in the direction of a pudendal cleft, yields the advantage of the curvature formed in the direction of a pudendal cleft working with that formed in the direction orthogonal to the pudendal cleft, thus rendering the exaggeration of the contour of a packed sanitary napkin more noticeable.

In such a case, when curvatures are formed in both directions, there is also yielded an advantage of the ability to considerably faithfully reproduce the curve of a so-called "hip guard" broadly covering the hips of the wearer. Further, when compared with a napkin curved in either the direction of a pudendal cleft or the direction orthogonal thereto; particularly, a napkin curved in the direction of the pudendal cleft, there is yielded the ability to enhance the three-dimensional appearance of the napkin even when the degree of the curvature is small. By virtue of such an advantage, the display of the invention contributes to space savings as compared with the case where a related-art single storage display is used.

In addition, as a result of curvatures being formed in both directions, a packed sanitary napkin is not offset in any of the longitudinal, lateral, and oblique directions. There is also yielded an advantage of a sample not being deviated, which would otherwise be caused when the single storage display is shaken by the consumer. This is very useful advantage for a single article storage type display which is often picked up and handled roughly by many consumers.

(3) The sample packing cover member defined in (1) or (2) is further characterized in that depressions and protrusions (depressions and protrusions following a contour of the human-body-contact surface; that is, human-body-contact surface depressions and protrusions) are further formed in the human-body-contact-side cover portion so as to follow a contour of the human-body-contact surface side of the product to be packed.

The sample packing cover member of (3) is further provided with depressions and protrusions following a contour of the packed product. As a result, an effect for enhancing the three-dimensional appearance of the sample packing cover member and prevention of displacement of the cover member with respect to the packed sanitary napkin are enhanced further, thereby further improving the function of the single article storage device (4) The sample packing cover member described in (1) or (2) is further characterized in that depressions and protrusions (depressions and protrusions which cause a person to recall the shape of a human body; that is, body-recall depressions and protrusions) are further formed in the human-body-contact-side cover portion, in order to cause a person to recall the shape of a portion of a human body which comes into contact with the contact surface of the product to be packed.

In the case of the sample packing cover member (4), depressions and protrusions which cause a person to recall the shape of a portion of a human body are formed in the human-body-contact surface. There is yielded an advantage of the consumer being able to recall a state in which the consumer wears the product, thus affording convenience at the time of selection of a product.

(5) The sample packing cover member described in (3) or (4) is further characterized by comprising, as an object which causes a person to artificially recall a portion of a human body, human-body-contact surface depressions and protrusions or a sub-display piece which can be fitted into the body-recall depressions and protrusions.

The sample packing cover member (5) is further provided with the sub-display piece, and hence the consumer can pick up the sub-display piece and fit the piece to the human-body-contact-side cover portion of the single article storage display. As a result, there is yielded an advantage of the consumer being able to more readily recall a state in which the consumer wears the sample product (that is a sanitary napkin) as compared with the case of the cover member (4).

(6) The sample packing cover member described any one of (1) through (5) is characterized by further comprising a support for pressing the product against the human-body-contact-side cover portion.

In the case of the sample packing cover member (6), the effect of exaggerating the sample product (that is a sanitary napkin) and the effect of prevention of displacement of the product, which stem from the three-dimensional sample packing cover member, are further enhanced by presence of the support in association with the pressing effect of the support.

(7) The sample packing cover member defined in any one of (1) through (6) is further characterized in that the entirety of the single article storage display, including the human-body-contact-side cover portion, is transparent.

In the case of the sample packing cover member (7), both front and back surfaces of the cover member are transparent. There is yielded an advantage of the consumer being able to more readily observe a sample product (that is a sanitary napkin) packed in the sample packing cover member.

(8) The sample packing cover member described in any one of (1) through (7) is further characterized in that a line simulating an underwear which will be or is to be brought into contact with the product is illustrated in a portion of the single article storage display (that is an underwear-contact-side cover portion), the portion covering a side (that is an underwear-contact-surface side) of the product which will act as a surface (an underwear contact surface) to come into contact with an underwear.

In the case of the sample packing cover member (8), addition of a line imitating an underwear enables the consumer to more readily recall a state in which the consumer actually wears an underwear. As a result, the consumer can determine an underwear suitable for use with the packed sample product (that is a sanitary napkin), on the basis of the imitation line.

(9) The sample packing cover member described in any one of (1) through (8) is characterized by further comprising an auxiliary display piece for pointing out an appealing point of the product.

The sample packing cover member (9) is further provided with an auxiliary display piece pointing out an appealing point of a sample product (for example, sanitary products, such as sanitary napkins, or incontinence products). As a result, the consumer can more readily determine appealing points of the sample product.

The auxiliary display piece itself is replaceable. A certain type of sample packing cover member can be doubly used for packing a plurality of types of sanitary napkins having different appealing points. In such a case, the cover member can be used for the sanitary napkins by means of replacing only the auxiliary display piece. First, a sample packing cover member which can be used for a plurality of types of sanitary napkins having different appealing points is prepared. Subsequently, a plurality of types of auxiliary display pieces are prepared. As a result, there is yielded an advantage of the sample packing cover member being readily used for every type of sanitary napkin without involvement a substantial impairment in a sales promotion effect.

(10) The sample packing cover member described in any one of (1) through (9) is further characterized in that the sampling packing cover member is an aperture-less sample packing cover member to be used for a portion of the product to be exposed outside the sample packing cover body.

The sample packing cover member (10) has no aperture for causing a portion of a product to become exposed outside. As a result, there can be prevented staining of a portion of the product, which would otherwise deteriorate the appearance of the product.

(11) The sample packing cover member defined in any one of (1) through (10) is further characterized in that, when a single article storage display for sales promotion purpose is formed as a result of the product being packed in the sample packing cover member, the display is formed to assume a shape such that a portion of the product which comes into contact with the buttocks of a wearer comes to an underside.

In the case of the sample packing cover member (11), when a single article storage display is suspended on a display case, a portion of a sample product to be attached to the front of a wearer comes to an upper position. When a consumer faces the front of the thus-suspended single article storage display, the orientation of the sample sanitary napkin; that is, the front and back of the napkin, is coincident with the direction in which the consumer actually wears the napkin on the genitals. Hence, the consumer can readily recall a state in which the thus-suspended sanitary napkin is fitted to the genitals as is. Thus, when compared with the related-art sample packing cover member, ease of selection of a product is enhanced.

(12) A sample packing cover member which acts as a cover of a single article storage display to be used for sales promotion of certain products, such as sanitary products or incontinence products, wherein, a portion of the cover member (a human-body-contact-side cover portion) which, when a certain product is packed, covers a side of the product (that is a human-body-contact surface side), the side acting as a contact surface (a human-body-contact surface) to be brought into contact with a wearer, is further provided with depressions and protrusions (depressions and protrusions following contours of the human-body-contact surface; that is, human-body-contact surface depressions and protrusions) which follow a contour of the human-body-contact surface side of the product to be packed; or depressions and protrusions (depressions and protrusions which cause a person to recall the shape of a human body; that is, body-recall depressions and protrusions) which cause a person to recall the shape of a portion of a human body, the portion coming into contact with the contact surface of the product to be packed.

The sample packing cover member (12) is further provided with depressions and protrusions matching a contour of a product to be packed. First, as in the case of the sample packing cover member (3), the three-dimensionally exaggeration effect and displacement prevention effect of the sample packing cover member for a packed sanitary napkin are further enhanced by depressions and protrusions following a contour of the product to be packed. The function of the single article storage display is enhanced much further.

In the sample packing cover member (12), depressions and protrusions which cause a person to recall the shape of a portion of a human body are formed in the human-body-contact-side cover portion. As in the case of the sample packing cover member (4), there is yielded an advantage of the consumer being able to recall a state in which the consumer wears the product, thus affording convenience at the time of selection of a product.

(13) The sample packing cover member defined in (12) is characterized by further comprising, as an object which causes a person to artificially recall a portion of a human body, the human-body-contact surface depressions and protrusions or a sub-display piece which can be fitted into the body recall depressions and protrusions.

As in the case of the sample packing cover member (5), the sample packing cover member (13) is further provided with the sub-display piece, and hence the consumer can pick up the sub-display piece and fit the piece to the human-body-contact-side cover portion of the single article storage display. As a result, there is yielded an advantage of the consumer being able to more readily recall a state in which the consumer wears the sample product (that is a sanitary napkin) as compared with the case of the cover member (4).

(14) A sample packing cover member which acts as a cover of a single article storage display to be used for sales promotion of certain sanitary products, wherein a line simulating underwear which will be or is to be brought into contact with the product is illustrated in a portion of the single article storage display (that is an underwear-contact-side cover portion), the portion covering a side (that is an underwear-contact-surface side) of the product which will act as a surface (an underwear contact surface) to come into contact with an underwear.

As in the case of the sample packing cover member (8), the sample packing cover body (14) is provided with a line imitating an underwear, which enables the consumer to more readily recall a state in which the consumer actually wears an underwear and to determine an underwear suitable for use with the packed sample product (that is a sanitary napkin), on the basis of the imitation line.

(15) A sample packing cover member which acts as a cover of a single article storage display to be used for sales promotion of certain products, further comprising an auxiliary display piece for pointing out an appealing point of the product.

As in the case of the sample packing cover member (9), the sample packing cover member (15) is further provided with an auxiliary display piece pointing out an appealing point of a sample product (for example, a sanitary product, such as a sanitary napkin, or an incontinence product). As a result, the consumer can more readily determine appealing points of the sample product.

(16) A sample packing cover member which acts as a cover of a single article storage display to be used for sales promotion of certain products, wherein, when a single article storage display for sales promotion purpose is formed as a result of the product being packed in the sample packing cover member, the display is formed to assume a shape such that a portion of the product which comes into contact with the buttocks of a wearer comes to an underside.

As in the case of the sample packing cover member (11), in the case of the sample packing cover member (16), when a single article storage display is suspended on a display case, a portion of a sample product to be attached to the front of a wearer comes to an upper position. When a consumer faces the front of the thus-suspended single article storage display, the orientation of the sample sanitary napkin; that is, the front and back of the napkin, is coincident with the direction in which the consumer actually wears the napkin on the genitals. Hence, the consumer can readily recall a state in which the thus-suspended sanitary napkin is fitted to the genitals as is. Thus, when compared with the related-art sample packing cover member, ease of selection of a product is enhanced.

(17) A single article storage display, in which a product corresponding to the sample packing cover body defined in any one of (1) through (16) is packed.

In the case of the single article storage display (17), a product is packed with the sample packing cover member described in any one of (1) through (16). As a result, the three-dimensionally exaggeration effect and displacement prevention effect of the sample packing cover member for a packed sample product (that is a sanitary product, such as a sanitary napkin, and an incontinence product) are further enhanced by depressions and protrusions following a contour of the product to be packed. The exaggeration of contour of the packed sanitary napkin becomes more noticeable. Further, even when a single article storage display is shaken intensively, there is yielded an advantage of preventing displacement of a packed sample.

There is also yielded an advantage of the consumer being able to recall a state in which the consumer wears the product. Further, the consumer can easily recall a state in which the consumer actually wears the product with an underwear. The sample can be used for determining an underwear suitable for use with a packed sample product (that is a sanitary napkin). Thus, the consumer can readily determine an appealing point of the product.

DETAILED DESCRIPTION OF THE PREFERRED EMBODIMENT

A preferred embodiment of the invention will be described by reference to the accompanying drawings. Here, a sanitary product (sanitary napkin) is used as an example of "product" in explanation of the preferred embodiment. However, the attributes of the invention are not changed depending on whether the product is a sanitary product or an incontinence product. Hence, the invention is not limited to an exemplified sanitary product.

Figure 1:
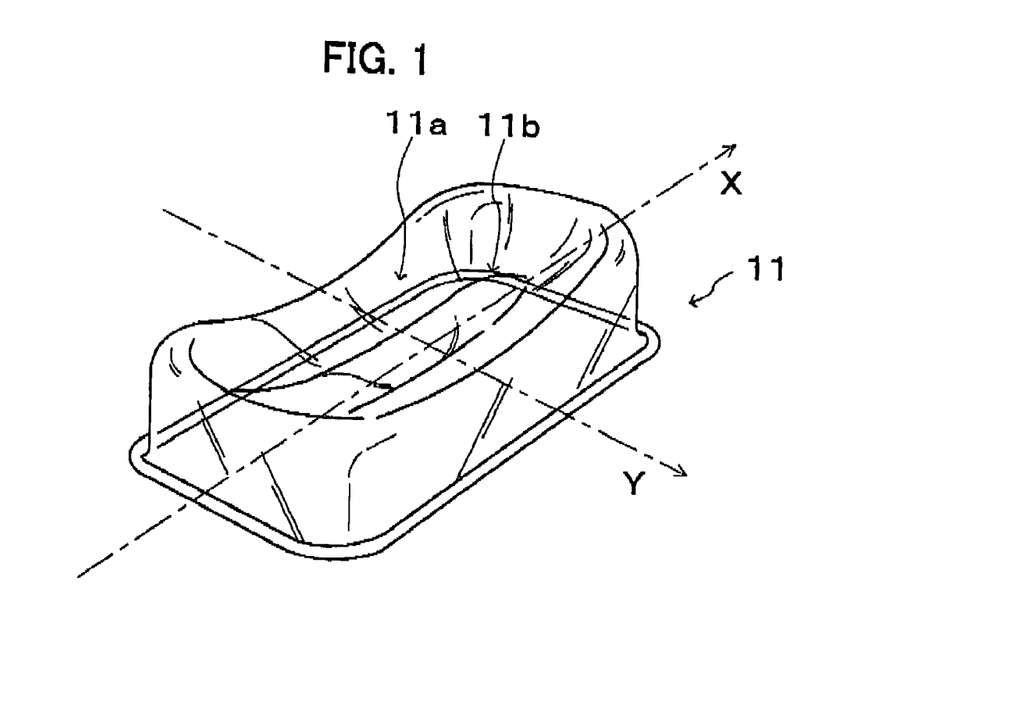
FIG. 1 is a perspective view showing a sample packing cover member according to a preferred embodiment of the invention.

FIG. 1 shows a sample packing cover body 11 for a single article storage display which is a preferred embodiment of the invention. A sanitary product 13 is packed in the sample packing cover body 11 which acts as a product sample, thereby forming a single article storage display 14 such as that shown in FIG. 2.

Figure 2:
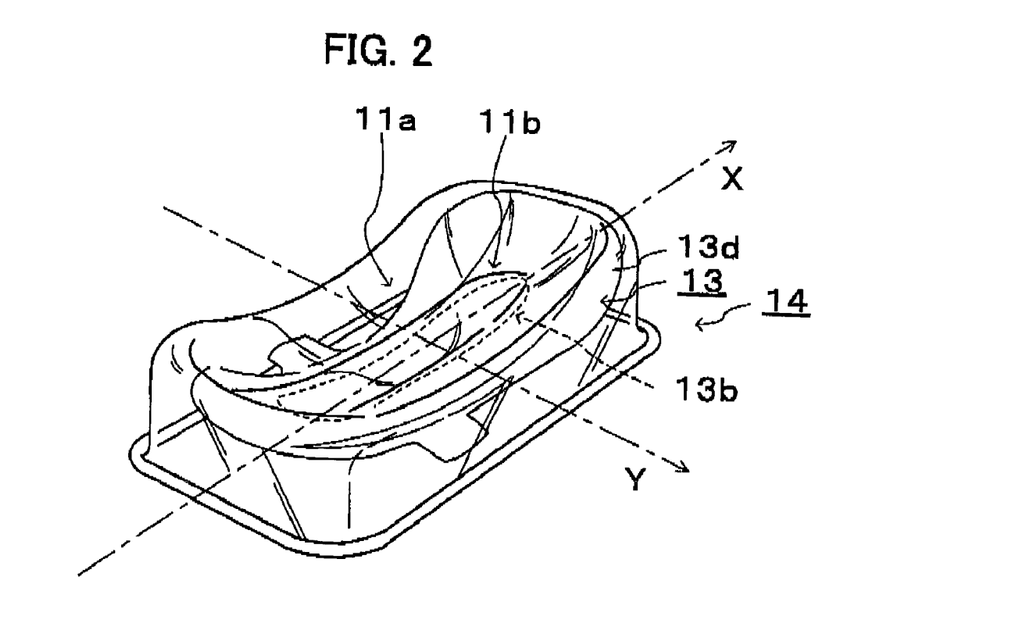
FIG. 2 is a perspective view of a single article storage display formed by packing a sample product (that is sanitary napkin) with a sample packing cover member of the preferred embodiment.

The ample packing cover member 11 of the invention is characterized in that an indentation 11a is formed in a direction (that is direction "y" shown in FIGS. 1 and 2) orthogonal to the direction of pudendal cleft of labia of a wearer (that is direction "x" shown in FIGS. 1 and 2). A curvature 11a is formed in the sample packing cover member 11 so as to give the impression that the entire single article storage display has a concave shape when the single article storage display 14 is viewed from the outside.

In the invention, the curvature is not indispensable in the direction "x" but in the direction "y." However, there is no necessity for the entire curvature to have a concave shape in the direction "y." In fact, in the embodiment, as shown in FIGS. 1 and 2, a protuberance 11b is formed in the center of the indentation 11a so as to correspond to a raised area 13b of an absorbent of the packed sanitary product 13.

Figure 3:
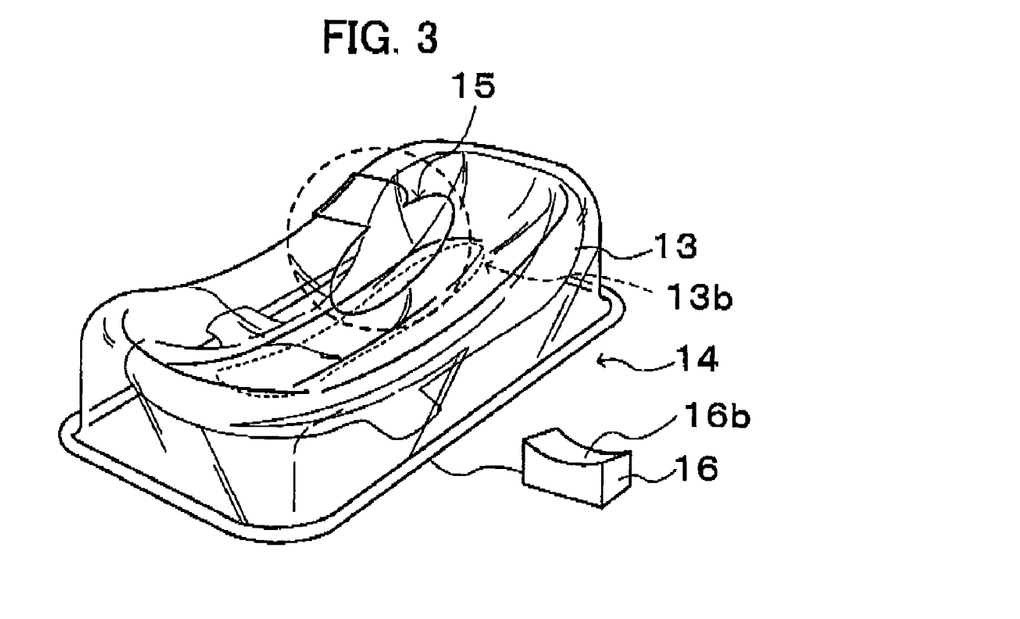
FIG. 3 is a perspective view showing an embodiment in which the cover member is provided with an auxiliary display piece.
Figure 4:
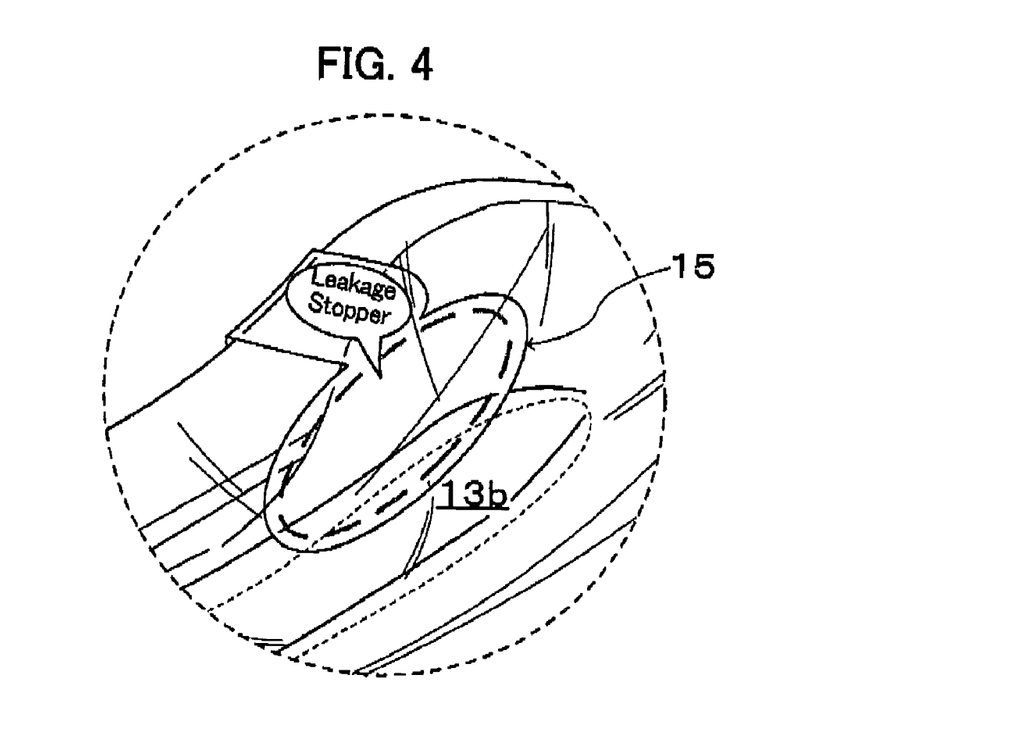
FIG. 4 is a fragmentary enlarged view of a portion of FIG. 3 for describing the auxiliary display piece.

As shown in FIG. 3, the single storage display of the invention has an auxiliary display 15 and a sub-display piece 16. FIG. 4 is a view of area "A" indicated by broken lines shown in FIG. 3 (that is the area of the display where the auxiliary display piece 15 is attached), which is enlarged for ease of comprehension.

As is evident from FIGS. 3 and 4, in the embodiment, the sample product is displayed by the auxiliary display piece 15 such that features of the sanitary product displayed in the single article storage display are highly appealed to consumers. The sanitary product 14 packed in the embodiment is a sanitary napkin for which considerable though is put into depressions and protrusions in the surface of the napkin for preventing backward leakage of menstrual blood. The sample packing cover member of the invention having curvatures (indentations) formed in both the directions "x" and "y" is suitable as a transparent case member for packing such a sanitary napkin.

In a further explanation, a raised (raised area) 13b formed in the center of the napkin is formed so as to fit the cleft of buttocks of a wearer so as to prevent backward leakage of menstrual blood (here, the raised area 13b is formed from absorbent or pulp for absorbing menstrual blood). As shown in FIGS. 3 and 4, the performance of the sanitary product is exaggerated by means of the auxiliary display piece 15.

As a result of the sub-display piece 16 being attached to the display, the consumer can ascertain fitting of the sample product by means of matching a small recess 16*a* of the sub-display piece 16 to a bulging section 11*b* of the sample packing cover member 11.

Figure 5:
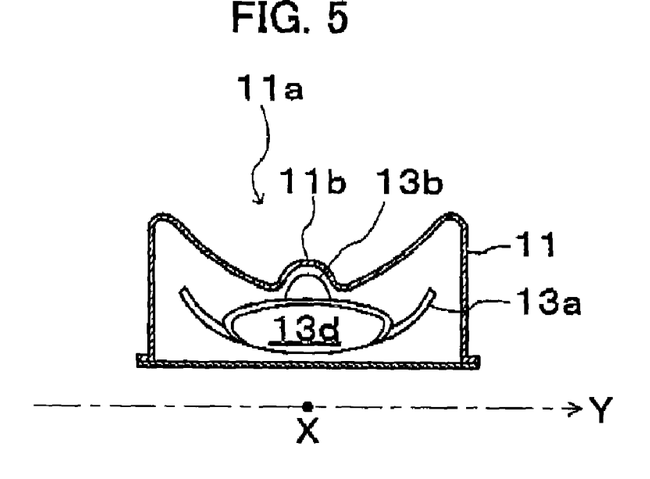
FIG. 5 is a fragmentary cross-sectional view of the single article storage display of the embodiment when the display is partially cut in direction "y"
Figure 6:
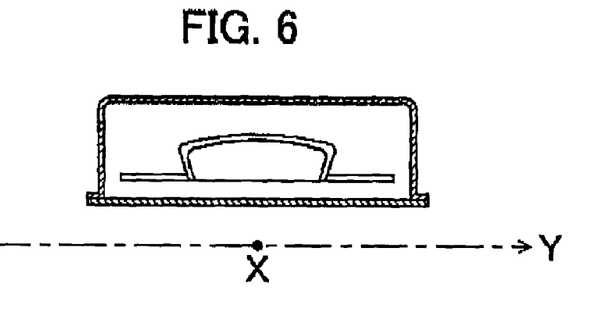
FIG. 6 is a fragmentary cross-sectional view of a related-art single article storage display when the display is cut at the same position as that shown in FIG. 5.

FIG. 5 is a fragmentary cross-sectional view of the display when cut in the direction "y" shown in FIG. 2. FIG. 6 is a fragmentary cross-sectional view of a related-art single article storage display which has hitherto been employed when the display is cut in the same direction.

As can be seen from a comparison between FIGS. 5 and 6, the single article storage display of the invention has a curvature in the direction "y" shown in FIG. 5. In contrast, the related-art single article storage display does not have any curvature such as that shown in FIG. 5. Hence, the sanitary product (napkin) 13 is housed in the sample packing cover 11 while flaps 13*a* are raised. As a result, the consumer examines purchase of a sanitary product can infer the effect of prevention of side leakage from the flaps 13*a* to a certain extent.

As is evident from FIG. 5, in the single article storage display of the invention, the raised area 13*b* of the napkin 13 is fitted into the bulging portion 11*b* of the sample packing cover member 11, thereby preventing lateral displacement (in the direction "y") of the napkin. In this regard, the related-art display shown in FIG. 6 fails to yield an advantage of prevention of side leakage of menstrual blood. As mentioned previously, the related-art display does not assume any construction which enables features of the packed sanitary product (napkin) 13 to be appealed to users in a readily, visually understandable manner. In this respect, the invention yields double effects; that is, an improvement in appeal of performance of a product and prevention of side leakage of menstrual blood, are achieved by means of a curvature formed in the direction "y."

Figure 7:
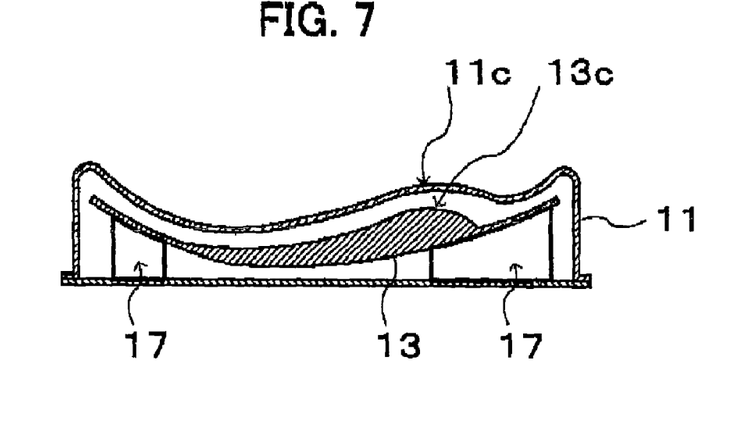
FIG. 7 is a fragmentary cross-sectional view of the single article storage display of the embodiment when the display is partially cut in direction "x"

As shown in FIG. 7, in a preferred embodiment, the contour of the cover body 11 is formed so as to follow the contour of the sanitary product (napkin) 13. As illustrated in FIG. 7, protrusions are formed in an upper surface 11*c* of the cover body 11 so as to follow depressions and protrusions in a surface 13*c* of the sanitary product (napkin) 13.

Figure 8:
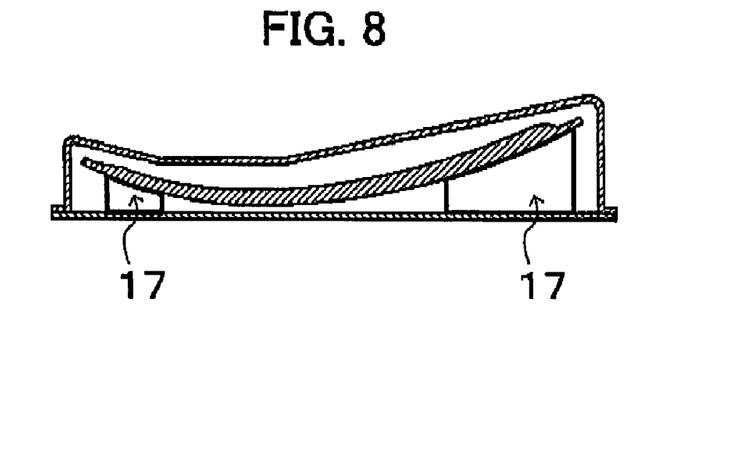
FIG. 8 is a fragmentary cross-sectional view of the related-art single article storage display when the display is cut at the same position as that shown in FIG. 7.

As a result, when compared with the case of the display having no such contrivance, such as that shown in FIG. 8, the shape of the cover member 11 matches that of the napkin 13. Even when the consumer cannot directly touch the sanitary product (napkin) 13 but can ascertain the contour of the product. Thus, the consumer can ascertain the contour of the surface of the sanitary product (napkin) 13 without involvement of direct touch on the product. The user can obtain a certain degree of assurance about the absorbing performance of the sanitary product stemming from the contour of the sanitary product (napkin) 13.

Depressions and protrusions formed in the upper surface 11*a* of the cover body 11 so as to follow depressions and protrusions in the surface 13*a* of the sanitary product (napkin) 13 are basically provided in both "x" and "y" directions for enhancing the three-dimensional feeding of the sanitary product (napkin) 13 and preventing sideway displacement of the napkin.

The sample packing cover body 11 of the embodiment is not particularly provided with an aperture (for example, an aperture 9 shown in FIGS. 13 and 14) for enabling direct contact with the packed napkin 13. Therefore, there is prevented staining of a portion of the product, which would otherwise be caused by intrusion of foreign matter into the aperture. Even if the sample packing cover body 11 of the embodiment is not provided with the aperture 9 such as that shown in FIGS. 13 and 14, the contour of the surface of the cover body 11 follows the contour of the surface of the napkin 13 as it is. Hence, the consumer can have assurance of absorbing performance stemming from the contour of the sanitary product 13 (napkin) to a certain extent, through ascertainment based on touching of the shape of the upper surface 11*c* of the cover body 11.

As shown in FIGS. 7 and 8, the display has a support table 17 for curving the packed sanitary product (napkin) 13 for exaggerating the three-dimensional profile of the product and retaining the shape.

Figure 9:
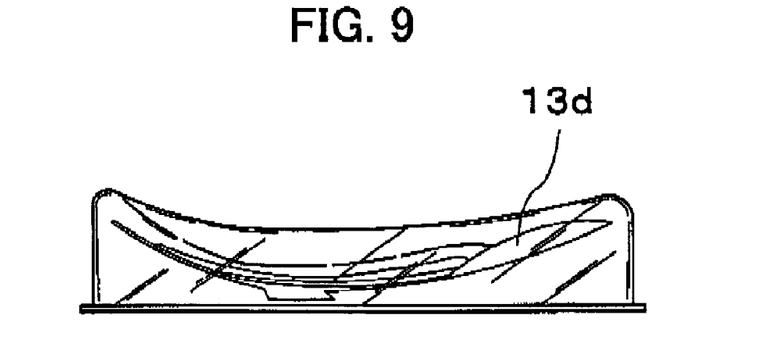
FIG. 9 is a side view of the single article storage display of the embodiment when the display is viewed in direction "y"
Figure 10:
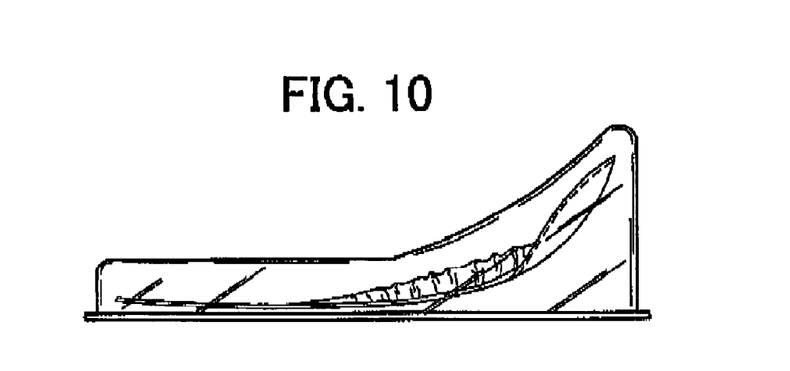
FIG. 10 is a side view of the related-art single article storage display when the display is viewed from the same position as that shown in FIG. 9.

FIGS. 9 and 10 are provided for describing the effect of the curvature of the invention. FIG. 9 shows a single article storage display of the invention. FIG. 10 shows a related-art single article storage display. As a matter of course, the curvature is formed in the direction "y" in FIG. 9. In contrast, no curvature is formed in the direction "y" in FIG. 10.

As shown in; for example, FIG. 9, the sample packing cover body 11 of the invention is curved in both "x" and "y" directions in a hip guard section 13*d*, where the napkin is to come into contact with buttocks. Hence, the overall cover body 11 has a concave shape and hence can readily reproduce a shape enclosing a hip (this becomes more clear by reference to FIG. 2). In contrast, the related-art product shown in FIG. 10 cannot reproduce the shape without involvement of a considerable increase in the degree of raise in the display in the direction "x."

Figure 11:
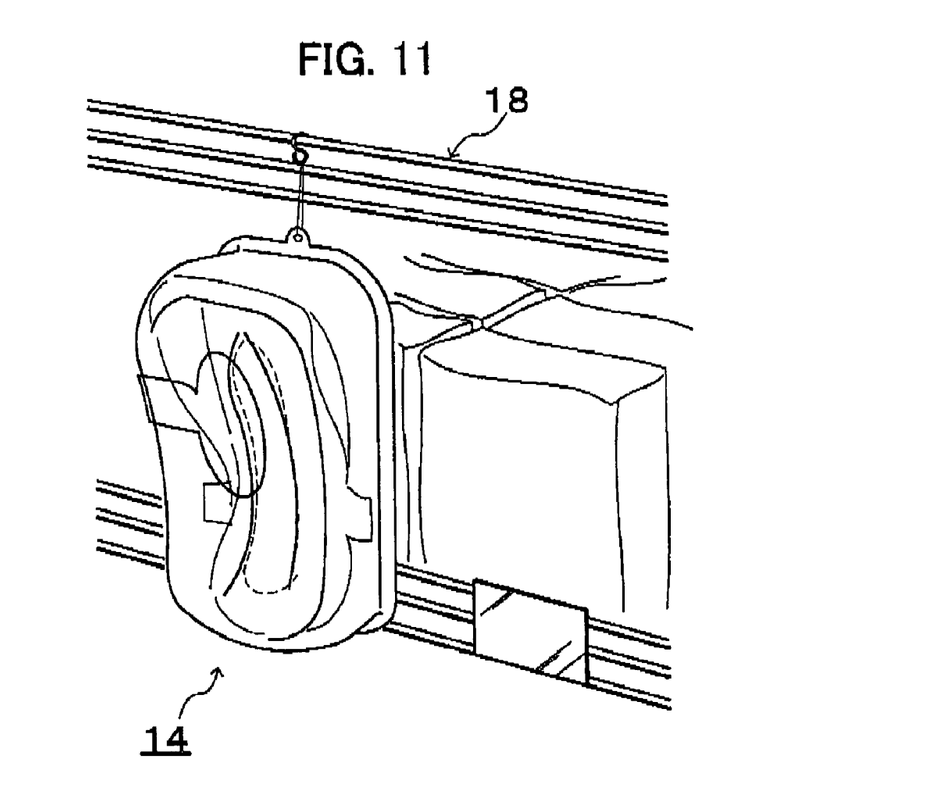
FIG. 11 is a view showing a single article storage display according to a preferred embodiment of the invention when the display is suspended on a showcase.

In such a case, a forward bulge in the display becomes greater. For instance, as shown in FIG. 11, the display may become interruptible when suspended on the display case 18. In contrast, in the case of the single article storage display 14 of the invention, the display does not occupy such an excessive area but becomes noticeable for customers but not interruptible.

As shown in FIG. 11, by means of the single article storage display, one selected from a package of commodity products is displayed independently. The customers can freely handle the display by hands. For this reason, the entirety of the cover body 11 is preferably transparent.

Plastics which are generally transparent, such as an acrylic resin or a polycarbonate resin, can be used as a transparent member. The member can be colored or provided with a pattern depending on the use of the member. The display can be freely observed by the customer while picking it up, turning it upside down, or turning its orientation. Even when the display is handled slightly violently, the sample is preferably not deviated within the packing cover body 11.

In this respect, the single article storage display 14 of the invention is curved longitudinally or laterally, whereby movement of the packed commodity product (that is the sanitary product or napkin 13) is regulated. Hence, the display is resistant to turning action performed by customers and remains displayed in its original form at all times. In this regard, the display can be considered to sufficiently fulfill the display function.

Figure 12:
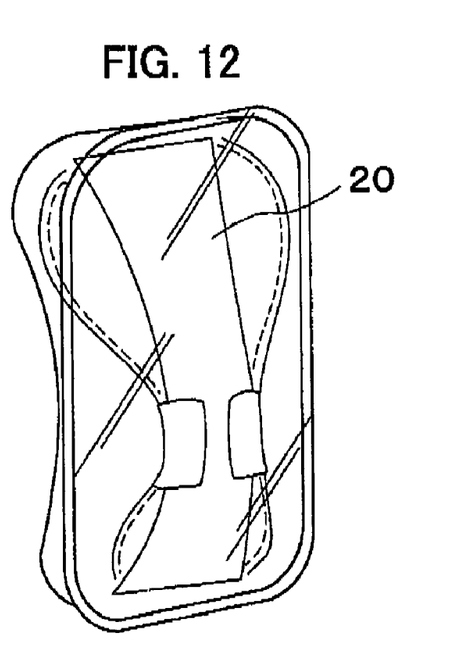
FIG. 12 is a view showing a single article storage display of the preferred embodiment when the display is provided with simulated underwear.

When the entire surface of the sample packing cover body 11 is made transparent, the consumer can ascertain a packed napkin from both front and back. As shown in FIG. 12, so long as a virtual piece 20; for example, shorts to which the napkin 13 is assumed to be attached, is enclosed in the display as a sample, thereby enabling the consumer to readily recall a situation in which the consumer wears the shorts.

As has been described, in the single article storage display of the invention, the performance and appealing points of an article can be provided to consumers to the extent possible.

Further, the invention can provide a sample packing cover body which enables production of such a single article storage display.

In short, the single article storage display of the invention is provided with curvatures (that is indentations) formed in both longitudinal and lateral directions. There is used a sample packing cover body whose contour matches that of a sample product (that is a sanitary product such as a sanitary napkin), and a sample product (that is a sanitary product such as a sanitary napkin) is packed in the cover body. As a result, an effect for enhancing the three-dimensional appearance of the packed sample product (for example, a sanitary product such as a sanitary napkin) and an effect for preventing displacement of the packed sample product are enhanced further. Exaggeration of the contour of the packed sanitary napkin is made more noticeable. There is yielded an advantage of the ability to prevent displacement of a packed sampled product, which would otherwise be caused when the single article storage display is intensively shaken by the consumer.

There is also yielded an advantage of the consumer being able to readily recall a situation in which the consumer wears a product. Thus, it becomes easy for the consumer to recall a situation in which the consumer actually wears the product. Further, an underwear suitable for use with a packed sample product (for example, a sanitary napkin) can be determined by the consumer. Thus, the customer can readily determine appealing points of the product.

What is claimed is:

1. A single article sales display cover for placement over a personal sanitary or incontinence product as a cover of a single article storage display for sales promotion of the personal product, the personal product being for use against a portion of a user's body, the personal product having a body-contact surface for contacting the user's body when in use, the personal product defining a lateral axis corresponding to a lateral direction on the user's body when in use, and the personal product defining a longitudinal axis along the user's body and normal to the lateral axis when in use, comprising:
    a cover member configured to receive the personal product with an inside of a transparent portion of the cover member covering and facing the body-contact side of the personal product;
    wherein an outside of the transparent portion forms a first curvature along the lateral axis such that the transparent portion, placed over the personal product, gives the impression of being concave around the longitudinal axis and the first curvature is formed to fit a shape of a pudendal cleft or the cleft of a buttocks; and
    wherein the sales display cover forms a line depicting an outline of underwear to be in contact with the product, the outline being depicted covering a side of the product intended to come into contact with underwear.

2. The sales display cover according to claim 1, wherein the outside of the transparent portion forms a second curvature along the longitudinal axis such that the transparent portion, placed over the personal product, gives the impression of being concave around the lateral axis.

3. The sales display cover according to claim 1, wherein the body-contact surface of the personal product defines depressions and protrusions forming a contour, and wherein:
    the transparent portion is configured with depressions and protrusions forming a contour conforming to the contour of the body contact surface of the personal product.

4. The sales display cover according to claim 3, and further comprising a sub-display piece configured to conform to the outer surface of the transparent portion and further configured in the form of a portion of a human body.

5. The sales display cover according to claim 1, wherein the transparent portion is configured with depressions and protrusions forming a contour simulating the contour of the portion of the user's body against which the personal product is to be used.

6. The sales display cover according to claim 5, and further comprising a sub-display piece configured to conform to the outer surface of the transparent portion and further configured in the form of a portion of a human body.

7. The sales display cover according to claim 1, and further comprising a support for pressing the product against the transparent portion.

8. The sales display cover according to claim 1, wherein the entirety of the single article storage display is transparent.

9. The sales display cover according to claim 1, and further comprising an auxiliary display piece for pointing out an appealing point of the product.

10. The sales display cover according to any one of claims 1 through 8, 9 or 4, wherein the cover member is free of an aperture exposing a portion of the personal product to contact from outside the cover member.

11. The sales display cover according to claim 1, wherein, with the personal product received inside the cover member, the cover member is shaped such that a portion of the product configured to come into contact with the buttocks of a wearer is displayed in a bottom end of the cover member.

12. A single article storage display, comprising:
    a sample packing cover body including the single article sales display cover defined in claim 1; and
    a personal product such as a sanitary product or an incontinence product packed within the sample packing cover body.

* * * * *